United States Patent
Hossler et al.

(10) Patent No.: US 8,524,458 B2
(45) Date of Patent: Sep. 3, 2013

(54) SECRETORY PROTEIN BIOMARKERS FOR HIGH EFFICIENCY PROTEIN EXPRESSION

(75) Inventors: Patrick Hossler, Westborough, MA (US); Ivan Correia, Winchester, MA (US)

(73) Assignee: Abbvie Inc., North Chicago, IL (US)

( * ) Notice: Subject to any disclaimer, the term of this patent is extended or adjusted under 35 U.S.C. 154(b) by 0 days.

(21) Appl. No.: 12/941,347

(22) Filed: Nov. 8, 2010

(65) Prior Publication Data

US 2011/0236906 A1 Sep. 29, 2011

Related U.S. Application Data

(60) Provisional application No. 61/259,527, filed on Nov. 9, 2009.

(51) Int. Cl.
*G01N 33/53* (2006.01)

(52) U.S. Cl.
USPC .......................................... 435/7.1; 436/518

(58) Field of Classification Search
None
See application file for complete search history.

(56) References Cited

U.S. PATENT DOCUMENTS

| | | | | |
|---|---|---|---|---|
| 5,302,517 A * | 4/1994 | Rhode, III | ..................... | 435/69.1 |
| 2005/0272055 A1 * | 12/2005 | Das et al. | .......................... | 435/6 |
| 2011/0143366 A1 * | 6/2011 | Schrattenholz | ................ | 435/7.1 |

FOREIGN PATENT DOCUMENTS

WO WO 2008/054514 5/2008

OTHER PUBLICATIONS

Martins de Lima, et al., "Identification of genes regulated by oleic acid in Jurkat cells by suppresive subtractive hybridization analysis", Database CA [Online], *Chemical Abstracts Service*, XP002617637, Database accession No. 142:49982 *Abstract, 2004.

Ryu, et al., "Gene expression profile in human HepG2 cells treated with naphthalene and its use for monitoring the enviroment pollution of the chemical", Database Chemabs [Online], *Chemical Abstracts Service*, XP002617638, Databse accession No. 151:352267 *Abstract, 2008.

Lambert, et al., "Proteomic analysis of wild type and luciferase reporter HepG2 cells exposed to TCDD", Database CA [Online], *Chemical Abstracts Service*, XP002617639, Database accession No. 154:26135 *Abstract, 2007.

Dinnis, et al., "Functional proteomic analysis of GS-NSO murine myeloma cell lines with varying recombinant monoclonal antibody production rate", *Biotechnology and Bioengineering*, vol. 94, No. 5, pp. 830-841, Aug. 5, 2006.

Nissom, et al., "Transcriptome and proteome profiling to understanding the biology of high productivity CHO cells", *Molecular Biotechnology, Humana Press, Inc.*, vol. 34, No. 2, pp. 125-140, Oct. 1, 2006.

Smales, et al., "Comparative proteomic analysis of GS-NSO murine myeloma cell lines with varying recombinant monoclonal antibody production rate", *Biotechnology and Bioengineering*, vol. 88, No. 4, pp. 474-488, Nov. 20, 2004.

Soussi, et al., "Stress proteins (Hsp72/73, Grp94) expression pattern in rat organs following metavanadate administration. Effect of green tea drinking", *Food and Chemical Toxicology*, vol. 44, No. 7, pp. 1031-1037, Jul. 1, 2006.

Trummer, et al., "Transcriptional profiling of phenotypically different Epo-Fc expressing CHO clones by cross-species microarray analysis", *Biotechnology Journal*, vol. 3, No. 7, pp. 924-937, Jul. 2008.

Wang, et al., "Co-expression of heat shock protein 70 and glucose-regulated protein 94 in human gastric carcinoma cell line BGC-823", *World Journal of Gastroenterology*, vol. 11, No. 23, pp. 3601-3604, Jun. 21, 2005.

Partial International Search Report for PCT/US2010/055953; International Filing Date: Nov. 9, 2010.

* cited by examiner

*Primary Examiner* — Jacob Cheu
(74) *Attorney, Agent, or Firm* — Baker Botts L.L.P.

(57) ABSTRACT

The instant invention relates to the field of protein production, and in particular is relates to compositions and processes for improving the production levels of recombinant proteins expressed in host cells.

16 Claims, 14 Drawing Sheets

Fractionated ER Microsomes      Fractionated Golgi

US 8,524,458 B2

SECRETORY PROTEIN BIOMARKERS FOR HIGH EFFICIENCY PROTEIN EXPRESSION

CROSS REFERENCE TO RELATED APPLICATION

This application claims the benefit of U.S. Provisional Application Ser. No. 61/259,527, filed Nov. 9, 2009, which is hereby incorporated by reference in its entirety.

INTRODUCTION

The instant invention relates to the field of protein production, and in particular relates to compositions and processes for improving the production levels of proteins expressed in host cells.

SEQUENCE LISTING

The specification further incorporates by reference the Sequence Listing submitted herewith via EFS on Mar. 5, 2013. Pursuant to 37 C.F.R. §1.52(e)(5), the Sequence Listing text file, identified as 0031681013SeqList.txt, is 3,544 bytes and was created on Mar. 5, 2013. The Sequence Listing, electronically filed herewith, does not extend beyond the scope of the specification and thus does not contain new matter.

BACKGROUND OF THE INVENTION

The production of recombinant proteins for biopharmaceutical applications typically involves the use of cell cultures having variable protein expression efficiencies. Advances in technologies for gene mapping, bio-imaging, and whole proteome analysis provide unique opportunities to understand many of the bottlenecks associated with the use of cell cultures for large-scale production of recombinant proteins. Numerous presentations at recent conferences (IBC-Antibody Development and Production, San Diego, Mar. 12-14, 2008), as well as publications in peer-reviewed journals (Gupta, P. and K. H. Lee (2007), "Genomics and proteomics in process development: opportunities and challenges" Trends Biotechnol 25(7): 324-30.) have demonstrated the utility of such technologies in the biopharmaceutical industry. The objectives for many of these studies include improving cell productivity, improving cell culture survival and proliferation, as well as introducing rapid and reliable techniques for the selection of high producing cell lines and real-time monitoring of the viability and physiology of the cells.

Even in light of the above-described advances, there remains a need in the art to identify biomarkers that correlate with high efficiency protein expression, particularly in the context of cell culture processes used for commercially produced recombinant bio-therapeutics. The instant invention addresses that need by providing secretory protein biomarkers that correlate with high efficiency protein expression

SUMMARY OF THE INVENTION

The present invention is directed to secretory protein biomarkers that correlate with high efficiency protein expression as well as methods of using such biomarkers to facilitate high efficiency protein expression, and especially recombinant protein expression, in host cells.

In certain embodiments the secretory protein biomarker is an endoplasmic reticulum fraction-resident protein. In certain embodiments the secretory protein biomarker is a Golgi fraction-resident protein. In certain embodiments the secretory protein biomarker is derived from a total cell fraction. In certain embodiments the secretory protein biomarker is up-regulated in a high efficiency cell or cell culture. In certain embodiments the secretory protein biomarker is down-regulated in a high efficiency cell or cell culture In certain embodiments of the present invention, a secretory protein biomarker is employed to identify a high efficiency cell or cell culture. In certain embodiments multiple secretory protein biomarkers are employed to identify a high efficiency cell or cell culture. In certain embodiments the up-regulation of a secretory protein biomarker is employed to identify a high efficiency cell or cell culture. In certain embodiments the down-regulation of a secretory protein biomarker is employed to identify a high efficiency cell or cell culture. In certain embodiments where multiple secretory protein biomarkers are employed to identify a high efficiency cell or cell culture, all of secretory protein biomarkers are up-regulated. In other embodiments involving multiple secretory protein biomarkers, all of the secretory protein biomarkers are down-regulated. In yet further embodiments involving multiple secretory protein biomarkers, one or more of the secretory protein biomarkers is up-regulated while one or more of the secretory protein biomarkers is down-regulated.

DETAILED DESCRIPTION OF THE INVENTION

5.1 Definitions

Figure 1:
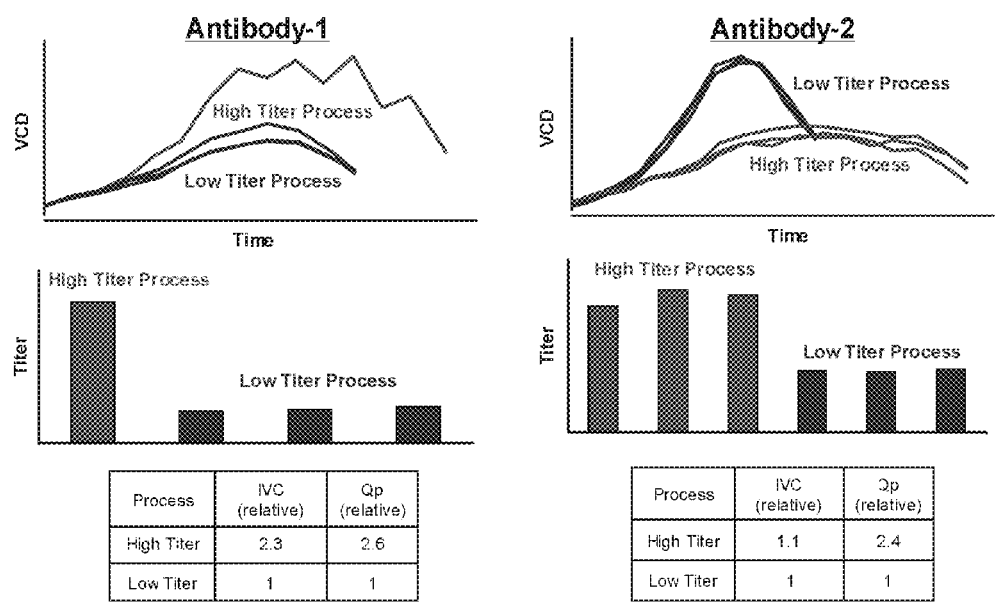
FIG. 1 depicts the effect of different cell culture treatments on product titers in development bioreactors. (IVC=integral of viable cell density, Qp=specific productivity).

As used herein, the term "high efficiency protein expression" refers to a phenotype of a cell or cell culture wherein the cell or cell culture expresses a protein of interest at a higher concentration than other comparable cells. This phenotype can be observed under general cell culture conditions or may require the use of particular cell culture conditions to elicit the phenotype. A cell manifesting high efficiency protein expression is referred to herein as a "high efficiency cell" and a culture of said cells is a "high efficiency cell culture."

As used herein, the term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. In certain embodiments the host cell is employed in the context of a cell culture.

As used herein, the term "cell culture" refers to methods and techniques employed to generate and maintain a population of host cells capable of producing a recombinant protein of interest, as well as the methods and techniques for optimizing the production and collection of the protein of interest. For example, once an expression vector has been incorporated into an appropriate host, the host can be maintained under conditions suitable for high level expression of the relevant nucleotide coding sequences, and the collection and purification of the desired recombinant protein. Mammalian cells are preferred for expression and production of the recombinant of the present invention, however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

As used herein a "recombinant expression vector" can be any suitable recombinant expression vector, and can be used to transform or transfect any suitable host. For example, one of ordinary skill in the art would appreciate that transformation or transfection is a process by which exogenous nucleic acid such as DNA is introduced into a cell wherein the transformation or transfection process involves contacting the cell with the exogenous nucleic acid such as the recombinant expression vector as described herein. Non-limiting examples of such expression vectors are the pUC series of vectors (Fermentas Life Sciences), the pBluescript series of vectors (Stratagene, LaJolla, Calif.), the pET series of vectors (Novagen, Madison, Wis.), the pGEX series of vectors (Pharmacia Biotech, Uppsala, Sweden), and the pEX series vectors (Clontech, Palo Alto, Calif.).

As used herein, the term "recombinant protein" refers to a protein produced as the result of the transcription and translation of a gene carried on a recombinant expression vector that has been introduced into a host cell. In certain embodiments the recombinant protein is an antibody, preferably a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., a Fc fragment or a Fab fragment).

As used herein, the term "secretory protein" refers to a protein resident, even transiently, in the secretory apparatus of a eukaryotic cell. The secretory apparatus of eukaryotic cells is composed of the endoplasmic reticulum (ER), the ER-Golgi intermediate compartment (ERGIC) Golgi apparatus (Ladinsky, et al. (1999), "Golgi structure in three dimensions: functional insights from the normal rat kidney cell" J Cell Biol 144(6): 1135-49), in addition to the vesicles involved in transport between them, as well as protein degradation mechanisms via the proteasome and lysosome. Electron microscopy and fractionation techniques have also been used to describe the major organelles of the secretory pathway (Sabatini, D. D. (1999), "George E. Palade: charting the secretory pathway" Trends Cell Biol 9(10): 413-7). A large number of proteins and other effector molecules are involved in secretory transport. Recently, researchers at McGill University have documented the presence of over 1400 proteins in the secretory pathway proteome (Gilchrist, A., C. E. Au, et al. (2006), "Quantitative proteomics analysis of the secretory pathway" Cell 127(6): 1265-81). The authors further demonstrated exquisite spatial information of the proteins in different compartments of the cell. Of the 1400 proteins identified, over 300 of them are of unknown function.

As used herein the term "endoplasmic reticulum" or "ER" refers to a eukaryotic cell organelle that forms an interconnected network of tubules, vesicles, and cisternae within cells that is involved in the production of phospholipids and proteins, among other functions. The ER facilitates proper protein folding and quality control (QC) for protein processing. During translation, proteins are translocated into the ER lumen after the signal recognition particle helps dock the translation complex to its receptor on the ER membrane. The nascent polypeptide is transferred to the translocon where it is subsequently passed into the lumen of the ER during peptide elongation, for proper folding and glycosylation within the highly oxidizing microenvironment. Cellular control mechanisms help prevent the transport of unfolded, misfolded, or unassembled proteins out of the ER. Protein folding and glycosylation initiation immediately take place in the ER after the polypeptide chain is translocated into the ER lumen. Through the concerted action of these proteins and others, a network of interactions occurs, and the molecular cargo is processed and screened. Numerous chaperone proteins facilitate protein folding, including heat shock proteins which temporarily block intermolecular interactions during folding, protein disulfide isomerase (PDI) which catalyzes the formation of correct disulfide bonds, and calnexin and calreticulin which serve as a quality control step towards ensuring that proteins are properly folded before leaving the ER (Hossler, P. (2006), "Experimental and Theoretical Exploration of Protein Glycosylation in Mammalian Cell Culture" Ph.D. Thesis ProQuest/UMI). Chaperone proteins are major ER-resident proteins for ensuring the proper folding structure of recombinant proteins. The most abundant ER chaperone is GRP78/BiP, which uses ATP hydrolysis to promote protein folding, and to prevent aggregation of unfolded proteins within the ER.

As used herein the term "Golgi apparatus" or "Golgi" refers to a compound membranous cytoplasmic organelle of eukaryotic cells, consisting of flattened, ribosome-free vesicles arranged in a more or less regular stack. Once proteins enter the Golgi apparatus, they are processed by a myriad of protein glycosylation enzymes. It is in the Golgi that the N- and O-glycans are further extended, further increasing the diversity of the glycoform profile. The first reactions for N-glycan processing are further removal of mannose sugars that are remaining from ER processing. After removal, a small number of glycosyltransferase enzymes react upon the glycans, but in variable order, leading to a diverse array of product glycans. This network of reactions, as well as the enzymatic substrate specificities has been documented previously (Hossler, P., L. T. Goh, et al. (2006), "GlycoVis: visualizing glycan distribution in the protein N-glycosylation pathway in mammalian cells" Biotechnol Bioeng 95(5): 946-60). This final glycoform profile has been shown to be affected by the nature of this network, as well as numerous other factors including the localization of the enzymes across the Golgi cisternae, relative nucleotide-sugar concentrations, and the protein residence time within the organelle.

As used herein, the term "up-regulated" refers to an increase in the amount of a particular composition, such as, but not limited to, a protein. Such increases in protein amount can be the result of, for example, but not by way of limitation: changes in transcription or translation rate of the DNA or mRNA, respectively, that encode the protein; changes in the stability of the mRNA that encodes the protein; and/or changes in the stability of the protein itself. In certain embodiments the increase in amount can be increases of about 1%, about 10%, about 25%, about 50%, about 100% or greater. In preferred embodiments, the increase in amount is an increase of at least about 100% to about 1,000%.

As used herein, the term "down-regulated" refers to an decrease in the amount of a particular composition, such as, but not limited to, a protein. Such decreases in protein amount can be the result of, for example, but not by way of limitation: changes in transcription or translation rate of the DNA or mRNA, respectively, that encode the protein; changes in the stability of the mRNA that encodes the protein; and/or changes in the stability of the protein itself. In certain embodiments the decrease in amount can be decreases of about 1%, about 10%, about 25%, about 50%, about 100% or greater. In preferred embodiments, the decrease in amount is a decrease of at least about 100% to about 1,000%.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

6.2 Biomarkers

The present invention is directed to secretory protein biomarkers that correlate with high efficiency protein expression as well as methods of using such biomarkers to facilitate high efficiency protein expression, and especially recombinant protein expression, in cells. Such biomarkers can be identified using a variety of techniques. For example, but not by way of limitation, proteomic analysis of a high efficiency cell cultures can be employed to identify secretory proteins exhibiting differential expression in high efficiency cell cultures as compared to lower efficiency cell cultures.

In order to identify a specific high efficiency cell or cell culture for use in the context of the instant invention, a cell or cells producing a protein of interest, for example a host cell or cells producing a recombinant protein of interest, can be cultured in a variety of different media to identify the media that elicits a high efficiency phenotype in the resulting cell culture (which comprises the original cell or cells and/or its/their progeny). Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985, the entire teachings of which are incorporated herein by reference, can be used as culture media for the cells. Any of these media types can be supplemented as necessary with hormones and/or other growth factors (such as, but not limited to, insulin, transferrin, or epidermal growth factor), salts (such as, but not limited to, sodium chloride, calcium, magnesium, and phosphate), buffers (such as, but not limited to, HEPES), nucleotides (such as, but not limited to, adenosine and thymidine), antibiotics (such as, but not limited to, gentamycin), trace elements (defined as inorganic compounds usually present at final concentrations in the micromolar range), and glucose or any equivalent energy source. Any other necessary supplements may also be included at appropriate concentrations that would be known to those skilled in the art.

In addition to variation of media type, other culture conditions, such as temperature, pH, and the like, can be modulated in an effort to elicit the high expression cell culture phenotype for use in the context of the instant invention. The type and extent of any particular change in such conditions that will be relevant for any one specific host cell will depend on the particular host cell selected for expression, and will be apparent to the ordinarily skilled artisan.

When using the cell culture techniques of the instant invention, the protein of interest can be produced intracellularly, in the periplasmic space, or directly secreted into the medium. In embodiments where the protein of interest is produced intracellularly, the particulate debris, either host cells or lysed cells (e.g., resulting from homogenization), can be removed by a variety of means, including but not limited to, by centrifugation or ultrafiltration. Where the protein of interest is secreted into the medium, supernatants from such expression systems can be first concentrated using a commercially available protein concentration filter, e.g., an Amicon™ or Millipore Pellicon™ ultrafiltration unit. The amount of the protein of interest used in determining whether a particular cell culture is a high efficiency cell culture can be calculated by assaying the media directly, in the case of secreted proteins, or by assaying media after the host cells have been lysed and the media has been subjected to centrifugation or ultrafiltration.

Once a high efficiency cell or cell culture has been identified, or conditions for high efficiency protein expression have been established, which result in a cell culture producing a protein of interest in a highly efficient manner, proteomic analysis can be undertaken to determine if there are specific proteins that are differentially expressed in the high efficiency cell culture as compared to a lower efficiency cell culture. The term "proteomic analysis" is used to refer to analysis of the expression pattern of one or more protein in a biological sample. Such analysis can, for example, be accomplished using mass spectrometry, two-dimensional gel electrophoresis, immunoassays, or by any other means for quantifying the level of protein expression in a sample.

Proteomic analysis can result in the identification of one or more proteins that are differentially expressed in high efficiency and low efficiency cell cultures. For example, but not by way of limitation such analysis can identify least 2, or at least 5 or at least 10 or at least 15, or at least 20, or at least 25, or at least 30, or at least 35, or at least 40, or at least 45, or at least 50, or at least 60, or at least 65, or at least 70, or at least 75, or at least 80, or at least 85, or at least 85, or at least 90, or at least 95, or at least 100, or at least 125, or at least 150, or at least 175, or at least 200 differentially expressed proteins in a particular cell culture sample.

Proteomic analysis may be directed toward a particular class of protein, for example, secretory proteins. In order to perform proteomic analysis of candidate secretory protein biomarkers, it is necessary to first obtain samples containing such proteins. In certain embodiments the candidate secretory protein biomarkers are obtained from total cell lysates. In preferred embodiments the candidate biomarker secretory proteins are obtained from samples enriched for secretory organelles. There are numerous well-established protocols reported in the literature for producing total cell lysates as well as for producing samples containing enriched (also referred to as "purified") secretory organelles, or subsets of such organelles. Typically, such protocols involve some form of cell disruption via chemical or mechanical means followed by differential, or density gradient centrifugation for purification and subsequent assessment. Other methods include the use of cell disruption followed by immunomagnetic separation via antibodies towards specific organelle proteins (Vitale, N., K. Horiba, et al. (1998), "Localization of ADP-ribosylation factor domain protein 1 (ARD1) in lysosomes and Golgi apparatus" Proc Nati Acad Sci USA 95(15): 8613-8). In certain embodiments, commercially available assay kits are employed, such as the Golgi Isolation Kit™ or the Endoplasmic Reticulum Isolation Kit™, both from Sigma-Aldrich, which utilize buffers and/or sucrose gradient ultracentrifugation to purify both the ER-containing and Golgi-containing fractions. In certain embodiments the source cells for such experiments can be obtained using small, large, or commercial scale bioreactors, for example, but not by way of limitation, 3 L benchtop Applikon bioreactors. In embodiments where specific organelles are purified, verification of organelle enrichment can be achieved using a variety of methods, including, but not limited to visual verification by transmission electron microscopy (TEM) morphometry.

Once a sample is prepared for proteomic analysis, the protein composition of that sample can be identified using a variety of means, including, but not limited to 2DGE. 2DGE is a well-established analytical method that can resolve 1000-2000 proteins in complex mixtures by their isoelectric points in the first dimension and then by their molecular weight using SDS-PAGE in the second dimension. Detection of proteins that are run on 2D gels can be accomplished by a number of different techniques, examples of which are disclosed at proteomeconsult.com. Silver staining is the most frequently used method for the detection of low abundance protein spots. Silver staining has good sensitivity (<1 ng protein/spot), however, a poor linear dynamic quantification range (~one order of magnitude). In contrast, Coomassie R-250 staining is more widely used, has a better linear dynamic quantification range (~two orders of magnitude), however, the sensitivity is low (~200 ng protein/spot). Coomassie G-250 staining offers higher sensitivity (~25 ng protein/spot) and is compatible with mass spectrometric procedures. Fluorescence staining has, with the introduction of SYPRO®-Ruby, become the choice for the 2D-gel based quantification of proteins. Sypro® Ruby staining offers good sensitivity (~1 ng protein/spot) and a linear dynamic quantification range of ~3 orders of magnitude. However, fluorescence stains add a significant amount of costs to the 2D-gel process. Finally, radio-labeling combines high sensitivity (<0.1 ng/spot) and high linear dynamic quantification range (4-5 orders of magnitude). However, increased effort has to be applied during gel handling, staining, scanning, storing and disposal to ensure operator safety and to comply with environmental regulations.

Key objectives in 2-D analysis are to remove subjectivity, to control variable gel running and gel image quality, to provide high sensitivity for low level protein expression, and to identify real changes in protein levels. Technology designed to meet these challenges has been developed by Nonlinear Inc. For example, Progenesis Discovery™ is a particular software solution specifically developed for researchers in the field of proteomics where large numbers of gels need to be accurately analyzed. Features of this software include Intelligent Noise Correction Algorithm (INCA), which controls the effect of image noise and drives accurate analysis, and Data Quality Control (Data QC), where the user receives a statistical measure of whether changes in spots are significant compared to the overall quality of the gel. The benefits of INCA and Data QC include high level of accuracy in spot detection, automated approach to 2D analysis and production of meaningful data from noisy images. In certain embodiments, differential expression is assigned using Progenesis software, followed by the physical excision of spots for mass spectrometry identification. In certain embodiments, the cut-off criteria that can be used for the assignment of differential expression is at least about a 2-fold, about a 3-fold, or about a 5-fold increase or decrease in normalized spot volume intensity from the 2D gels. In alternative embodiments, the cut-off criteria that can be used for the assignment of differential expression is a relative expression level between two culture conditions of (positive or negative) 0.01, 0.05, 0.10, 0.2, 0.4, 0.6, 0.8, or 1.0. In certain embodiments, relative expression can be determined using the following equation:

Relative Expression of Protein "$i$"=$\log_{10}$ [(Normalized Spot Volume)$_{i,\ culture\ 1}$/(Normalized Spot Volume)$_{i,\ culture\ 2}$]

Following the excision, the identity of the biomarker of interest can be obtained using a number of techniques, including, but not limited to, mass spectrometry. "Mass spectrometry" or "MS" refers to an analytical technique in which a sample to be analyzed is ionized and then introduced to produce differences based on mass using an electric or magnetic force, and thus the masses of ions are analyzed. There are variety of MS principles that can be used in connection with the instant invention including, but not limited to, ion trap MS, Fourier transform ion cyclotron resonance mass spectrometry (FT-ICR/MS), ion scanning MS, and Q-TOF MS. In the methods of the present invention, MS analysis can be performed using only one technique (that is, only one mass spectrometer), or by using a plurality of mass spectrometers that are linked to each other, where such analysis is referred to as "MS/MS analysis".

In certain embodiments, the specific type of mass spectrometry employed is nano-flow ESI Q-TOF MS/MS analysis. Electrospray ionization (ESI) is a technique for transporting biomolecules diluted in a liquid into a gaseous phase. This desolvation method is customarily used for mass-spectrometry identification of proteins. For example, protoeolytic enzymes are employed to digest proteins into unique peptide segments. These segments are then separated through reverse-phase High-Pressure-Liquid-Chromatography (HPLC) and sequentially electro-sprayed into a mass spectrometer. By determining the amino acid sequence of specific peptide segments, the mass-spectrometer yields sufficient information to identify the protein with high confidence. The fundamental physics of the ESI process has been the subject of numerous investigations (for reviews of recent development in this field, see Bruins A. P., "Mechanistic aspects of electrospray ionization," Journal of Chromatography A, vol. 794, pp. 345-347, 1998; and Cech et al., "Practical implications of some recent studies in electrospray ionization fundamentals," Mass Spectrometry Reviews, vol. 20, pp. 362-387, 2001). An electrospray produces a cloud of ions in the gaseous phase. In a nano-ESI mode favored for applications in proteomics, the electrospray is established by pumping an analyte solution at slow flow rates (100-1000 nl/min) through a small bore capillary placed within a high electric field. This specific mass spectrometry technique can be coupled with the use of various software programs, such as, but not limited to, Spectrum Mill software (Agilent), for identification of the biomarker in the SwissProt database.

Specific, non-limiting examples of secretory biomarkers modulated in a high efficiency cell or cell line are set forth in Table 1.

TABLE 1

Examples of Secretory Biomarkers

| | |
|---|---|
| Endoplasmin precursor (GRP 94) | 26S Proteasome non ATP-ase regulatory subunit 13/SH3 domain GRB2-like protein B1/COP9 sinalosome complex subunit 4 |
| Seryl-tRNA synthetase | Cytoplasmic dynein 1 intermediate chain |
| Dihydrolipolylysine residue acetyltransferase/ methionineaminopeptidase 2 | Ribosome Binding Protein 1 |
| F-actin capping protein subunit alpha 2 | Alcohol Dehydrogenase (NADP+) |
| 60s acidic ribosomal protein PO | Glutamate dehydrogenase 1 (mitochondrial precursor) |
| Heterogeneous nuclear ribonucleoprotein K | Proteasome activator complex subunit 1 |
| Eukaryotic translation initiation factor 3 subunit 7 | Cytoplasmic 2, Actin |
| Endoplasmin precursor (GRP 94) | Annexin A5/Coatomer subunit Epsilon |
| Elongation factor 1 beta | Glucosidase 2 |
| Seryl-tRNA synthetase/RAS GTPase-activating protein binding 2 | Triosephosphate isomerase |
| Eukaryotic translation factor 3 subunit 3 | Heterogeneous nuclear ribonucleoprotein F |
| Pre mRNA processing factor 19/T-complex protein 1 subunit bet | Sorting Nexin 6/Synaptic vesicle membrane VAT-1 homolog |
| Elongation factor 1 gamma | 14-3-3 protein zeta/delta |
| Tubulin gamma-1 chain/Eukaryotic translation initiation factor 2 subunit 2 | Vimentin/Tubulin alpha-2 chain |
| Myosin regulatory light chain | Vaculoar ATP Synthase |
| Guanine nucleotide binding protein subunit beta 1 | Ig-G gamma-1 chain C |
| 26S Protease regulatory subunit 6B | Protein disulfide isomerase A-6 precursor/ Protein NDRG1 (N-myc downstream-regulated gene 1 protein) |
| Eukaryotic peptide chain releases factor subunit 1 | 60 kDa heat shock protein, mitochondrial precursor (Hsp60) |
| Protein disulfide isomerase A-3 precursor | T-complex protein 1 subunit epsilon |
| Tubulin alpha-2 | UPF0027 protein |
| Endoplasmin precursor (GRP 94) | |

Additional exemplary biomarkers include, but are not limited to, EH-Domain Containing Protein 4; Heat Shock Protein Beta 1; Translation Initiation Factor 3 Subunit 3; ATP Synthase Subunit Beta; 60S Acidic Ribosomal Protein PO; Ezrin; Nucleophosmin; Calreticulin; 14-3-3 Protein Gamma; Septin-11; Annexin A2; ADP-Ribosylation Factor-Like Protein 2R; Heat Shock Cognate 71 kDa Protein; Myosin Light Polypeptide 6; and Major Vault Protein.

According to particular non-limiting embodiments of the invention, at least one, or at least two, or at least three, or at least four, or at least five, or at least ten, optionally up to five, up to ten, or up to twenty, or up to thirty, or up to forty, or up to forty-six of said above-described secretory protein biomarkers (where more than one biomarker is referred to as a "panel") can be used to identify a high efficiency cell or cell culture.

In certain embodiments, such panels include, but are not limited to, one, two, three, four, five, six, seven, or all eight of: EH-Domain Containing Protein 4; Heat Shock Protein Beta 1; Myosin Regulatory Light Chain; Guanine Nucleotide Binding Protein Beta 1; Translation Initiation Factor 3 Subunit 3; Vimentin; ATP Synthase Subunit Beta; and Elongation Factor 1 Gamma. In certain of such embodiments, EH-Domain Containing Protein 4; Heat Shock Protein Beta 1; Myosin Regulatory Light Chain; and/or Guanine Nucleotide Binding Protein Beta 1 are up-regulated, while Translation Initiation Factor 3 Subunit 3; Vimentin; ATP Synthase Subunit Beta; and/or Elongation Factor 1 Gamma are down-regulated.

In certain embodiments, such panels include, but are not limited to, one, two, three, four, five, six, seven, or all eight of: EH-Domain Containing Protein 4; Heat Shock Protein Beta 1; Myosin Regulatory Light Chain; Guanine Nucleotide Binding Protein Beta 1; Translation Initiation Factor 3 Subunit 3; Vimentin; ATP Synthase Subunit Beta; and/or Elongation Factor 1 Gamma. In certain embodiments EH-Domain Containing Protein 4; Heat Shock Protein Beta 1; Myosin Regulatory Light Chain; and/or Guanine Nucleotide Binding Protein Beta 1 are up-regulated, while Translation Initiation Factor 3 Subunit 3; Vimentin; ATP Synthase Subunit Beta; and/or Elongation Factor 1 Gamma are down-regulated.

In certain embodiments, such panels include, but are not limited to, one, two, three, four, five, six, seven, or all eight of: EH Domain-Containing Protein 4; 60S Acidic Ribosomal Protein PO; Heterogeneous Nuclear Ribonucleoprotein K; Ezrin; ATP Synthase Subunit Beta; Nucleophosmin; Vimentin; and/or Calreticulin. In certain embodiments, EH Domain-Containing Protein 4; 60S Acidic Ribosomal Protein PO; Heterogeneous Nuclear Ribonucleoprotein K; and/or Ezrin are up-regulated, while ATP Synthase Subunit Beta; Nucleophosmin; Vimentin; and/or Calreticulin are down-regulated.

In certain embodiments, such panels include, but are not limited to, one, two, three, four, five, six, or all seven of: 14-3-3 Protein Gamma; Protein Disulfide Isomerase A3 Precursor; Septin-11; Annexin A2; ADP-Ribosylation Factor-Like Protein 2R; Heat Shock Cognate 71 kDa Protein; and/or Myosin Light Polypeptide 6. In certain embodiments 14-3-3 Protein Gamma; Protein Disulfide Isomerase A3 Precursor; Septin-11; Annexin A2; and/or ADP-Ribosylation Factor-Like Protein 2R are up-regulated, while Heat Shock Cognate 71 kDa Protein; and/or Myosin Light Polypeptide 6 are down-regulated.

In certain embodiments, such panels include, but are not limited to, one, two, or all three of: Heat shock cognate 71 kDa protein; Major Vault Protein; and/or Eukaryotic Translation Initiation. Factor5A-1. In certain embodiments, Heat shock cognate 71 kDa protein; Major Vault Protein; and/or Eukaryotic Translation Initiation Factor5A-1 are down-regulated.

In certain embodiments, such panels include, but are not limited to, one, two, or all three of: Guanine Nucleotide-Binding Protein (SEQ ID No. 2); Heat Shock Protein Beta-1; and/or 14-3-3 Protein Zeta/Delta. In certain embodiments Guanine Nucleotide-Binding Protein (SEQ ID No. 2) is down-regulated, while Heat Shock Protein Beta-1; and/or 14-3-3 Protein Zeta/Delta are up-regulated.

In certain embodiments, the expression level of the biomarker, or biomarkers, being analyzed will be measured at a specific point during the culture process. For example, but not by way of limitation, the expression level of the biomarker, or biomarkers, can be assayed on Day1, Day 2, Day 3, Day 4, Day 5, Day 6, Day 7, Day 8, Day 9, Day 10, Day 11, Day 12, Day 13, Day 14, or Day 15 of the cell culture process. In certain embodiments the expression of the biomarker, or biomarkers, will be assayed at one, two, three or more points during the cell culture process. In certain embodiments, particular biomarkers need not all be assayed at all time points, but rather certain biomarkers can be assayed at certain time points and other biomarkers assayed at other, not necessarily completely overlapping, time points.

In related, specific, non-limiting embodiments, the present invention provides for kits for identifying modulation in expression of one or a panel of said above-listed secretory protein biomarkers. Such kids can, for example, comprise a detectable antibody directed against said biomarker or biomarkers and a means for detecting said antibody. In non-limiting specific embodiments, in a panel provided in said kit, biomarkers listed above represent up to about 20 percent, or up to about 30 percent, or up to about 50 percent, or up to about 75 percent, or up to about 90 percent, or up to about 100 percent, of biomarkers in the entire panel to be tested. Said kit may optionally further comprise one or more positive and/or one or more negative control sample(s).

6.3 Methods of Using Biomarker Compositions

In certain embodiments of the present invention, one or more protein biomarker, preferably one or more secretory protein biomarker, is employed to identify a high efficiency cell or cell culture. Such identification is often useful in the context of commercial scale-up of recombinant protein production. For example, but not by way of limitation, an initial, small scale cell culture is initiated to promote the efficiency of recombinant protein production. This can be facilitated by monitoring the expression level of one or more secretory protein biomarker that is/are associated with high efficiency expression of the protein of interest. In certain embodiments, it is the up-regulation of a secretory protein biomarker that is employed to identify a high efficiency cell culture. In alternative embodiments it is the down-regulation of a secretory protein biomarker that is employed to identify a high efficiency cell culture. In preferred embodiments, multiple secretory protein biomarkers are employed to identify a high efficiency cell culture. In such embodiments where multiple secretory protein biomarkers are employed, all of the biomarkers can be up-regulated, all of the secretory protein biomarkers can be down-regulated, or one or more of the secretory protein biomarkers is up-regulated while one or more of the secretory protein biomarkers is down-regulated In alternative embodiments of the present invention, the secretory protein biomarker is employed to monitor the expression efficiency of an established large-scale cell culture, such as a commercial cell culture. In such embodiments periodic monitoring of one or more secreted protein biomarkers can ensure that the cell culture is continuing to exhibit the high efficiency cell culture phenotype. In certain examples, a change in the expression of the biomarker can indicate a need to adjust one or more cell culture conditions, such as, but not limited to, media type, temperature, and pH. In certain embodiments it is the up-regulation of a secretory protein biomarker that is employed to identify a high efficiency cell culture. In alternative embodiments it is the down-regulation of a secretory protein biomarker that is employed to identify a high efficiency cell culture. In preferred embodiments, multiple secretory protein biomarkers are employed to identify a high efficiency cell culture. In such embodiments where multiple secretory protein biomarkers are employed, all of the biomarkers can be up-regulated, all of the secretory protein biomarkers can be down-regulated, or one or more of the secretory protein biomarkers.

6.4 High Efficiency Cells and Cell Cultures

The present invention further provides for a high efficiency cell or cell culture which manifests a biomarker profile associated with high efficiency protein expression. In particular, the present invention provides for a high efficiency cell or cell culture which manifests a secretory biomarker profile associated with high efficiency protein expression. For example, and not by way of limitation, said cell or cell culture exhibits a modulation of the expression of one or more secretory protein biomarker set forth in Tables 1-7.

According to particular non-limiting embodiments of the invention, expression of at least one, or at least two, or at least three, or at least four, or at least five, or at least ten of the above-listed secretory biomarkers may be modulated in a cell or cell culture of the invention. In a specific, non-limiting embodiment of the invention, said cell is a CHO cell.

EXAMPLES

7.1 Example 1

7.1.1 Organelle F Ractionation

Two Chinese Hamster Ovary (CHO) cell lines producing recombinant glycoproteins of interest were employed throughout the following examples. Both cell lines were shown to produce g/L levels of the desired product, but that culture conditions facilitating large increases in product titers (FIG. 1). Comparing differences in secretory pathway protein levels using the same clone but under these different culture conditions allowed for findings as to what differences exist at the cellular level using cells that have the same genetic makeup and gene amplification levels.

Figure 2:
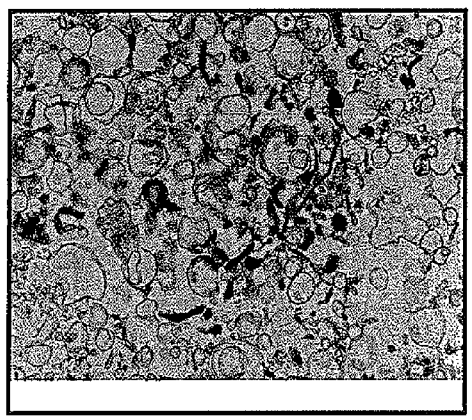
FIG. 2 depicts Transmission Electron Microscopic (TEM) images of purified ER and Golgi fractions.
Figure 2:
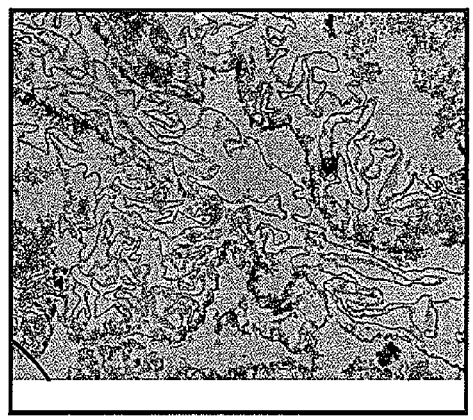

To determine the relative distribution of candidate biomarker secretory proteins inside the organelles of the recombinant protein producer cell lines, it was necessary to first purify these organelles. There are numerous well-established protocols for organelle purification reported in the literature. Typically, such protocols involve some form of cell disruption via chemical or mechanical means followed by differential, or density gradient centrifugation for purification and subsequent assessment. Other methods include the use of cell disruption followed by immunomagnetic separation via antibodies towards specific organelle proteins (Vitale, N., K. Horiba, et al. (1998). "Localization of ADP-ribosylation factor domain protein 1 (ARD1) in lysosomes and Golgi apparatus." Proc Nati Acad Sci USA 95(15): 8613-8). In the instant example, commercially available assay kits, which utilized proprietary buffers and/or sucrose gradient ultracentrifugation to purify both the ER and Golgi. The source cells for these experiments came from 3 L benchtop Applikon bioreactors, from which a large number of source cells were generated for organelle fractionation. Any yield limitations of the assay were more than compensated for by the large number of cells that were generated. Verification of organelle enrichment was achieved using visual verification by transmission electron microscopy (TEM) morphometry. (FIG. 2).

Figure 3:
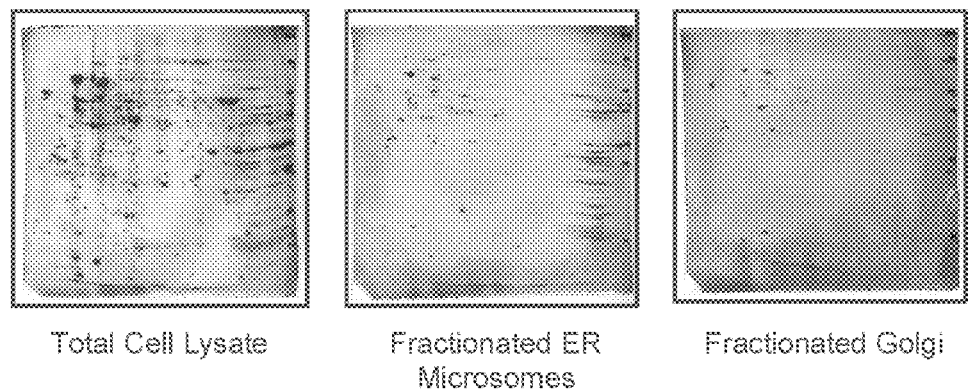
FIG. 3 depicts 2D-gel electrophoresis of total cell lysates versus fractionated ER and Golgi samples.

7.1.2. Differential Mapping of the Secretory Process by Two-Dimensional Gel Electrophoresis The organelle enrichment described in Example 1 was followed by 2D gel electrophoresis (2DGE) (FIG. 3). 2DGE is a well-established analytical method that can resolve 1000-2000 proteins in complex mixtures by their isoelectric points in the first dimension and then by their molecular weight using SDS-PAGE in the second dimension. Detection of proteins that are run on 2D gels can be accomplished by a number of different techniques, including the silver staining technique employed in the gels included in FIG. 3

Key objectives in 2-D analysis are to remove subjectivity, to control variable gel running and gel image quality, to provide high sensitivity for low level protein expression, and to identify real changes in protein levels. Technology designed to meet these challenges has been developed by Nonlinear Inc, including the Progenesis software. For the instant samples, differential expression was assigned using Progenesis software, followed by the physical excision of spots for mass spectrometry identification. The cut-off criteria used for the assignment of differential expression was at least a 2-fold increase or decrease in normalized spot volume intensity from the 2D gels on at least 1 of the time course samples in either the ER or Golgi enriched fractions.

Figure 4:
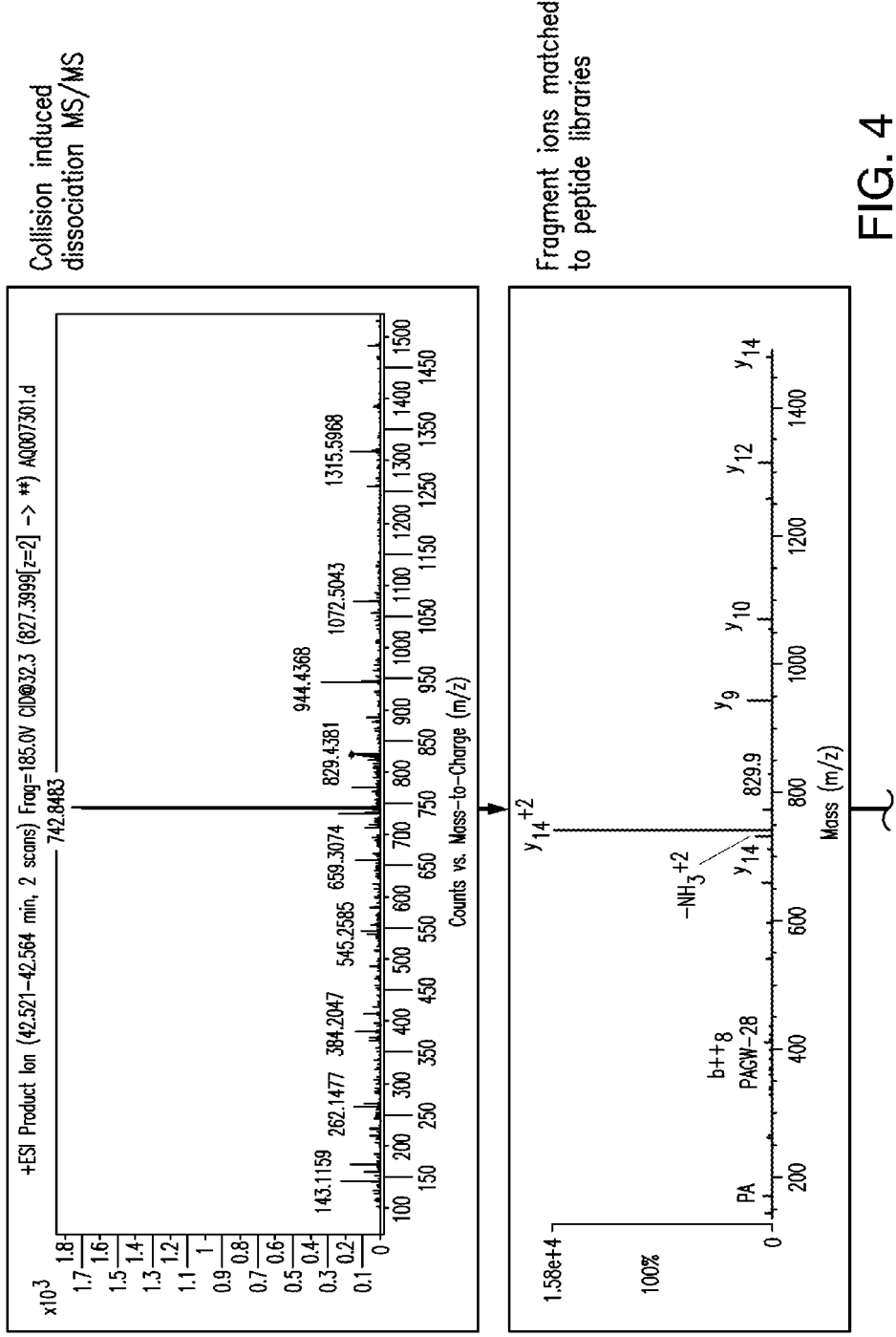
FIG. 4 depicts a mass spectrometry workflow diagram for identification of differentially expressed protein spots excised from 2D gels.
Figure 4:
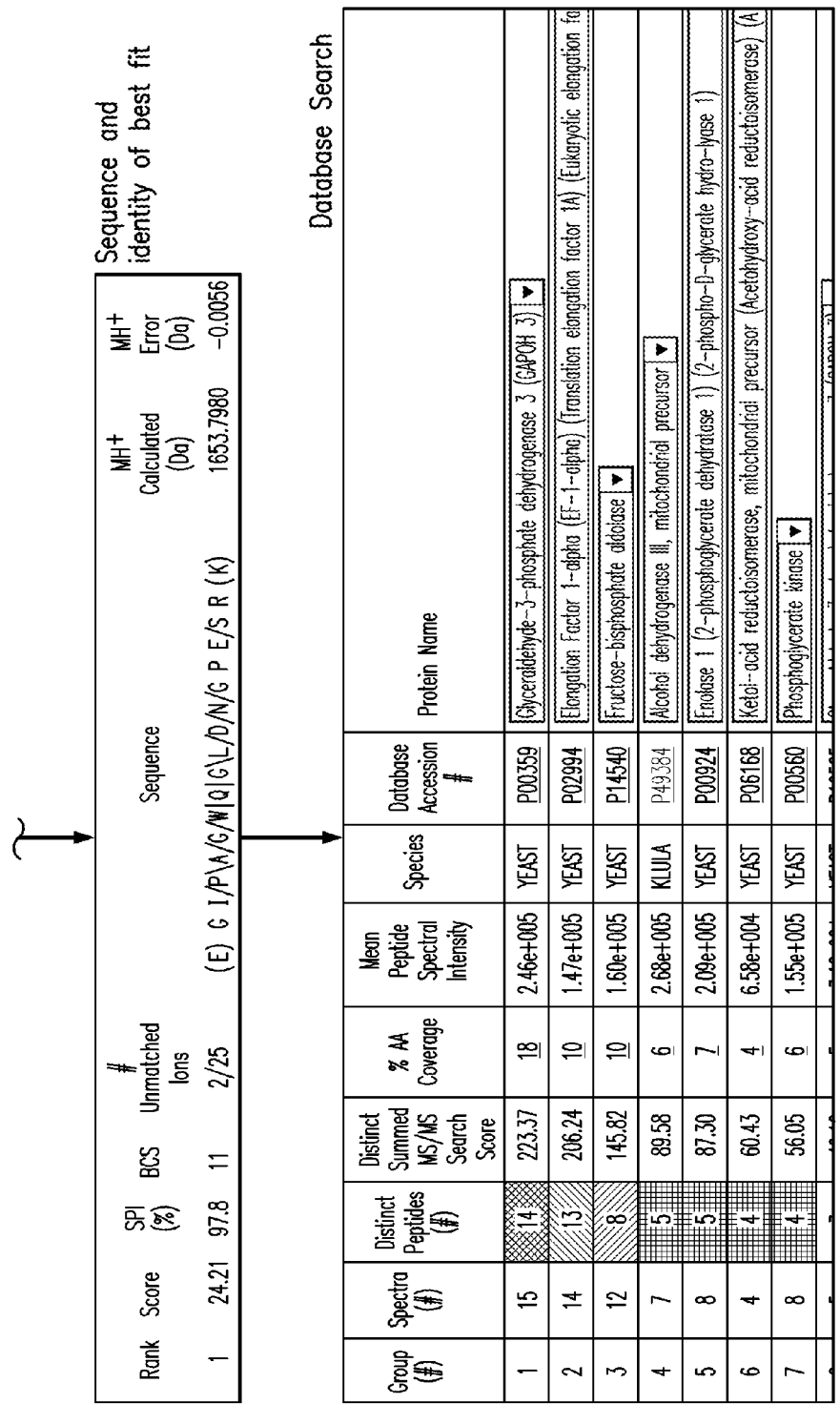

7.1.3. Mass Spectrometry (MS) Analysis of Differentially Expressed Proteins The protein spots identified and excised in Example 6.1.2., were then processed using Nano-flow ESI Q-TOF MS/MS analysis to identify the particular biomarker secretory proteins. Individual protein assignments were made using Spectrum Mill software (Agilent), and the SwissProt database (FIG. 4). Table 1, in Section 6.2 above, lists the biomarker secretory proteins having differential expression of at least a 2-fold increase or decrease in normalized spot volume intensity from the 2D gels on at least 1 of the time course samples in either the ER or Golgi enriched fractions that could be subsequently identified using mass spectrometric analysis.

7.2 Example 2

7.2.1. Comparison of Three Distinct Protein-Producing Cell Lines

This example describes a comparison of three distinct protein producing cells lines cultured under media having differing richness levels as well as a comparison of complex media versus defined media. The cell culture, organelle isolation, protein analysis, and protein identification was performed as described in Example 1, sections 7.1.1.-7.1.3. above, unless described otherwise.

7.2.2. Cell Line 1 Analysis

Figure 5:
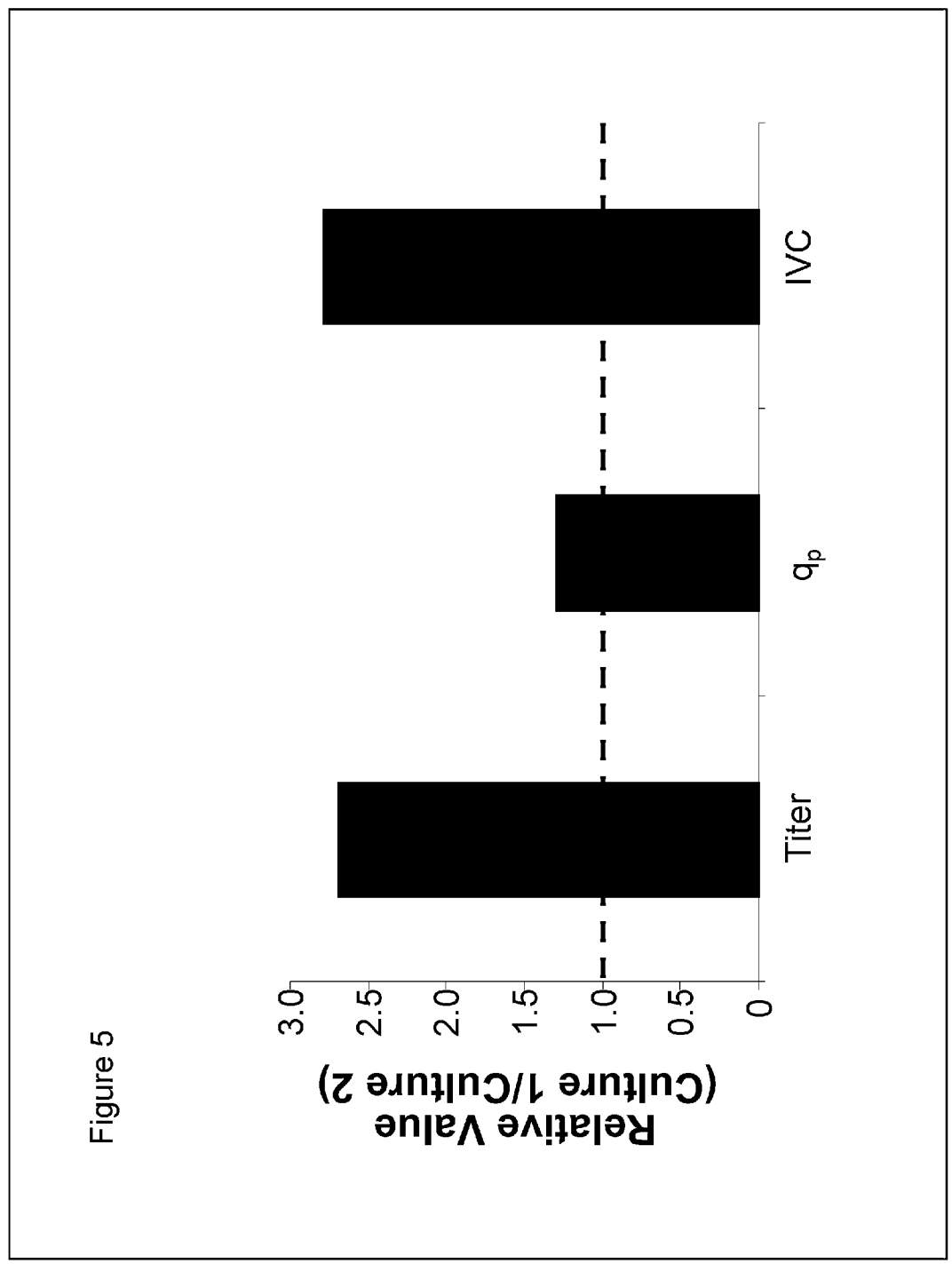
FIG. 5 depicts the relative value (Culture 1/Culture 2) of the product titer, specific productivity ($q_p$), and integral of viable cell density (IVC) obtained during the culture processes of Cell Line 1 described in Section 7.2.2.
Figure 6:
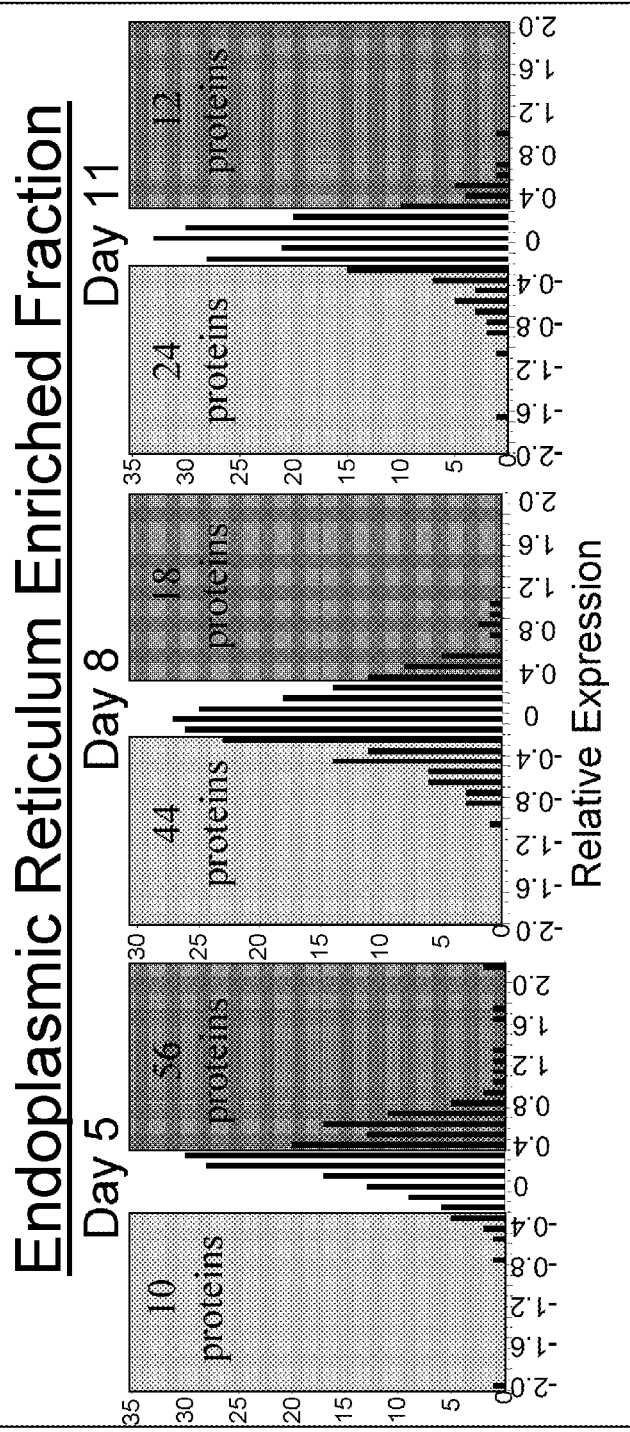
FIG. 6 depicts the relative expression (x-axis) versus number of proteins (y-axis) falling either less than −0.4 or greater than 0.4 in endoplasmic reticulum enriched fraction samples taken at days 5, 8, and 11 from the culture processes of Cell Line 1 described in Section 7.2.2.
Figure 7:
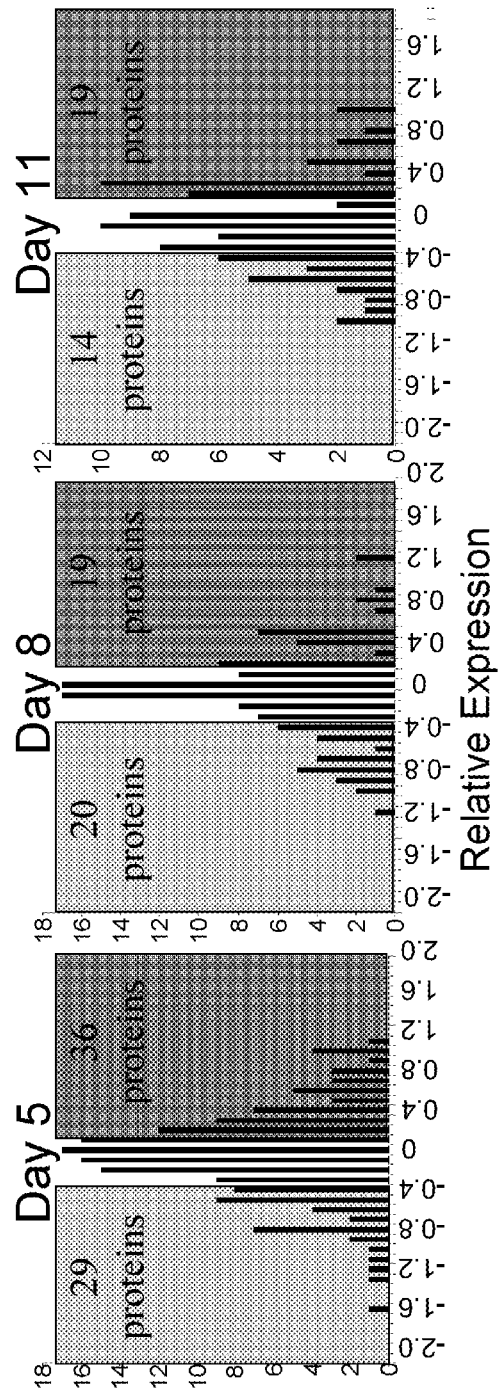
FIG. 7 depicts the relative expression (x-axis) versus number of proteins (y-axis) falling either less than −0.4 or greater than 0.4 in golgi enriched fraction samples taken at days 5, 8, and 11 from the culture processes of Cell Line 1 described in Section 7.2.2.

Cell Line 1 was cultured using two distinct process modes and two distinct culture media. Culture 1 of Cell Line 1 employed a fedbatch process mode and a complex, rich media. In contrast, Culture 2 of Cell Line 1 employed a batch process mode and a complex, lean media. The relative values (Culture 1/Culture 2) of the product titer, specific productivity ($q_p$), and integral of viable cell density (IVC) for the Cell Line 1 comparison are provided in FIG. 5. To identify differentially expressed proteins samples of each culture were taken on Days 5, 8, and 11, and these samples were analyzed by 2-D gel electrophoresis. Summary data relating to the differentially expressed proteins is presented in FIG. 6 (Endoplasmic Reticulum Enriched Fraction) and 7 (Golgi Enriched Fraction). Specific proteins identified as differentially expressed are presented in Table 2 (Endoplasmic Reticulum Enrich Fraction) and Table 3 (Golgi Enriched Fraction).

TABLE 2

Cell Line 1; Exemplary Differentially Expressed Proteins - ER Fraction

| Representative Proteins | Relative Expression (Sample Day) | Function |
| --- | --- | --- |
| EH-Domain Containing Protein 4 | 0.94 (8) | Protein Transport |
| Heat Shock Protein Beta 1 | 0.79 (8) | Cellular Stress Response |
| Myosin Regulatory Light Chain | 0.61 (5) | Cellular Organization |
| Guanine Nucleotide Binding Protein Beta 1 | 0.56 (5) | Signaling |
| Translation Initiation Factor 3 Subunit 3 | −0.46 (8) | Protein Translation |
| Vimentin | −0.70 (11) | Cellular Organization |
| ATP Synthase Subunit Beta | −0.70 (11) | Metabolism |
| Elongation Factor 1 Gamma | −0.83 (8) | Protein Translation |

TABLE 3

Cell Line 1; Exemplary Differentially Expressed Proteins - Golgi Fraction

| Representative Proteins | Relative Expression (Sample Day) | Function |
| --- | --- | --- |
| EH-Domain Containing Protein 4 | 0.94 (8) | Protein Transport |
| Heat Shock Protein Beta 1 | 0.79 (8) | Cellular Stress Response |
| Myosin Regulatory Light Chain | 0.61 (5) | Cellular Organization |
| Guanine Nucleotide Binding Protein Beta 1 | 0.56 (5) | Signaling |
| Translation Initiation Factor 3 Subunit 3 | −0.46 (8) | Protein Translation |
| Vimentin | −0.70 (11) | Cellular Organization |
| ATP Synthase Subunit Beta | −0.70 (11) | Metabolism |
| Elongation Factor 1 Gamma | −0.83 (8) | Protein Translation |

7.2.3. Cell Line 2 Analysis

Figure 8:
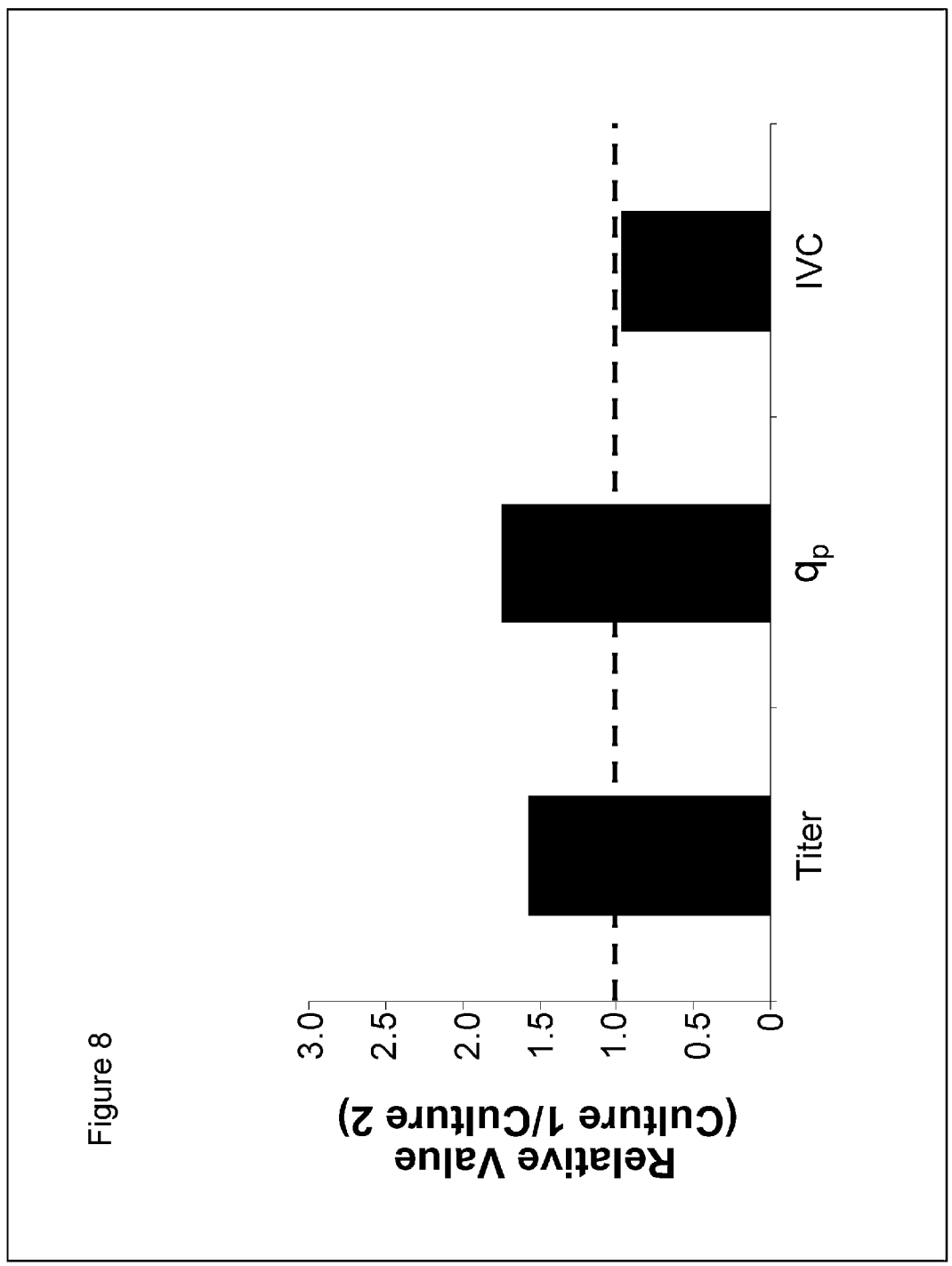
FIG. 8 depicts the relative value (Culture 1/Culture 2) of the product titer, specific productivity ($q_p$), and integral of viable cell density (IVC) obtained during the culture process of Cell Line 2 described in Section 7.2.3.
Figure 9:
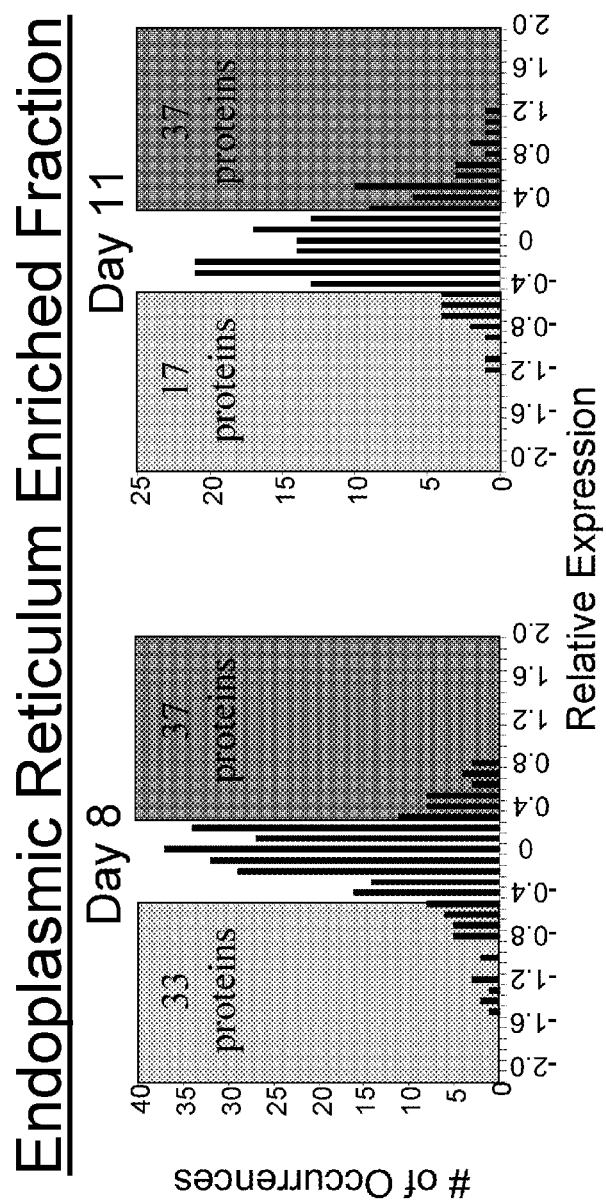
FIG. 9 depicts the relative expression (x-axis) versus number of proteins (y-axis) falling either less than −0.4 or greater than 0.4 in endoplasmic reticulum enriched fraction samples taken at days 8 and 11 from the culture processes of Cell Line 2 described in Section 7.2.3.
Figure 10:
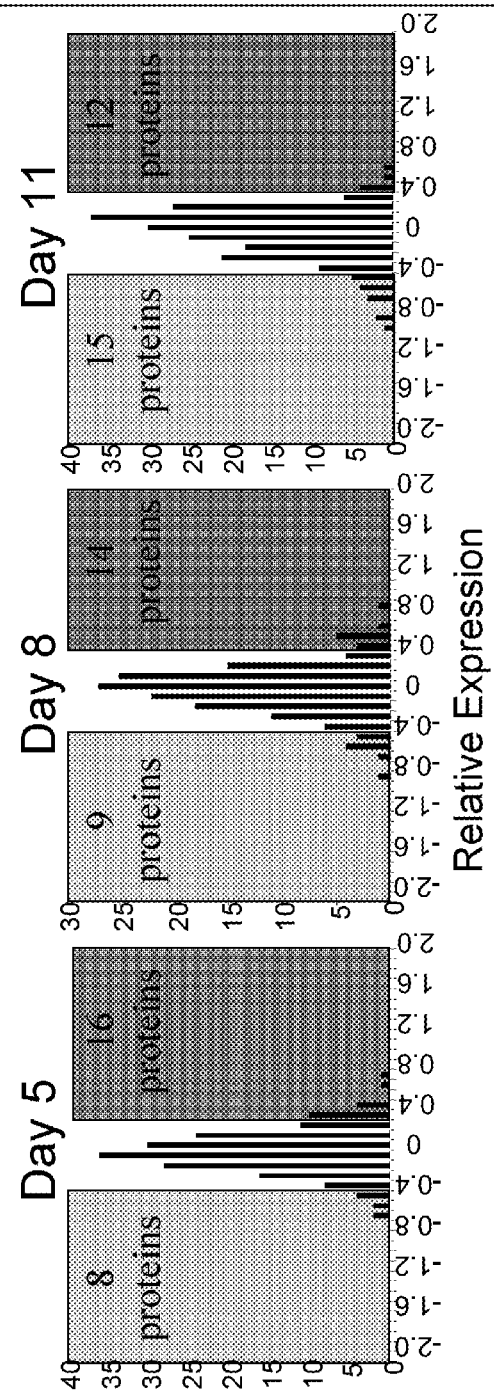
FIG. 10 depicts the relative expression (x-axis) versus number of proteins (y-axis) falling either less than −0.4 or greater than 0.4 in golgi enriched fraction samples taken at days 5, 8, and 11 from the culture processes of Cell Line 2 described in Section 7.2.3.

Cell Line 2 was cultured twice using the same batch process, but with distinct culture media. Culture 1 of Cell Line 2 employed a complex, rich media, while Culture 2 employed a complex, lean media. The relative values (Culture 1/Culture 2) of the product titer, specific productivity ($q_p$), and integral of viable cell density (IVC) for the Cell Line 2 comparison are provided in FIG. 8. To identify differentially expressed proteins samples of each culture were taken on Days 8, and 11 (Endoplasmic Reticulum Enriched Fractions) and Days 5, 8, and 11 (Golgi Enriched Fractions), and these samples were analyzed by 2-D gel electrophoresis. Summary data relating to the differentially expressed proteins is presented in FIGS. 9 (Endoplasmic Reticulum Enriched Fraction) and 10 (Golgi Enriched Fraction). Specific proteins identified as differentially expressed are presented in Table 4 (Endoplasmic Reticulum Enrich Fraction) and Table 5 (Golgi Enriched Fraction).

TABLE 4

Cell Line 2; Exemplary Differentially Expressed Proteins - ER Fraction

| Representative Proteins | Relative Expression (Sample Day) | Function |
| --- | --- | --- |
| EH Domain-Containing Protein 4 | 0.80 (8) | Protein Transport |
| 60S Acidic Ribosomal Protein PO | 0.72 (11) | Protein Translation |
| Heterogeneous Nuclear Ribonucleoprotein K | 0.60 (8) | mRNA Processing |
| Ezrin | 0.58 (8) | Cellular Organization |
| ATP Synthase Subunit Beta | −0.41 (11) | Metabolism |
| Nucleophosmin | −0.57 (11) | Protein Translation |
| Vimentin | −0.73 (11) | Cellular Organization |
| Calreticulin | −1.13 (11) | Protein Folding |

TABLE 5

Cell Line 2; Exemplary Differentially Expressed Proteins - Golgi Fraction

| Representative Proteins | Relative Expression (Sample Day) | Function |
| --- | --- | --- |
| 14-3-3 Protein Gamma | 0.69 (8) | Signaling |
| Protein Disulfide Isomerase A3 Precursor | 0.68 (5) | Protein Folding |
| Septin-11 | 0.66 (11) | Cellular Organization |
| Annexin A2 | 0.58 (8) | Signaling |
| ADP-Ribosylation Factor-Like Protein 2R | 0.46 (5) | Protein Processing |
| Heat Shock Cognate 71 kDa Protein | −0.64 (5) | Protein Folding |
| Myosin Light Polypeptide 6 | −0.67 (5) | Cellular Organization |

7.2.4. Cell Line 3 Analysis

Figure 11:
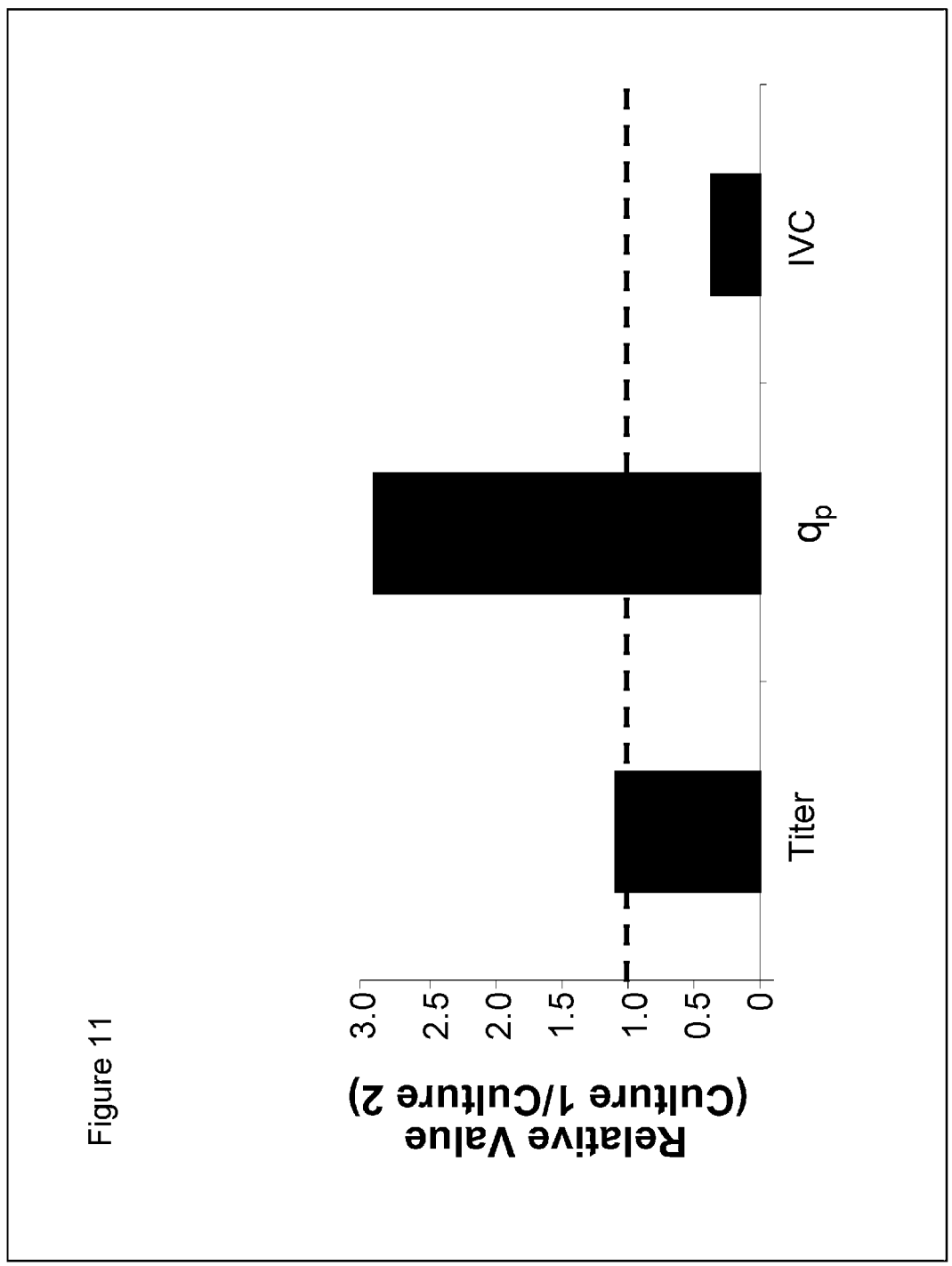
FIG. 11 depicts the relative value (Culture 1/Culture 2) of the product titer, specific productivity ($q_p$), and integral of viable cell density (IVC) obtained during the culture process of Cell Line 3 described in Section 7.2.4.
Figure 12:
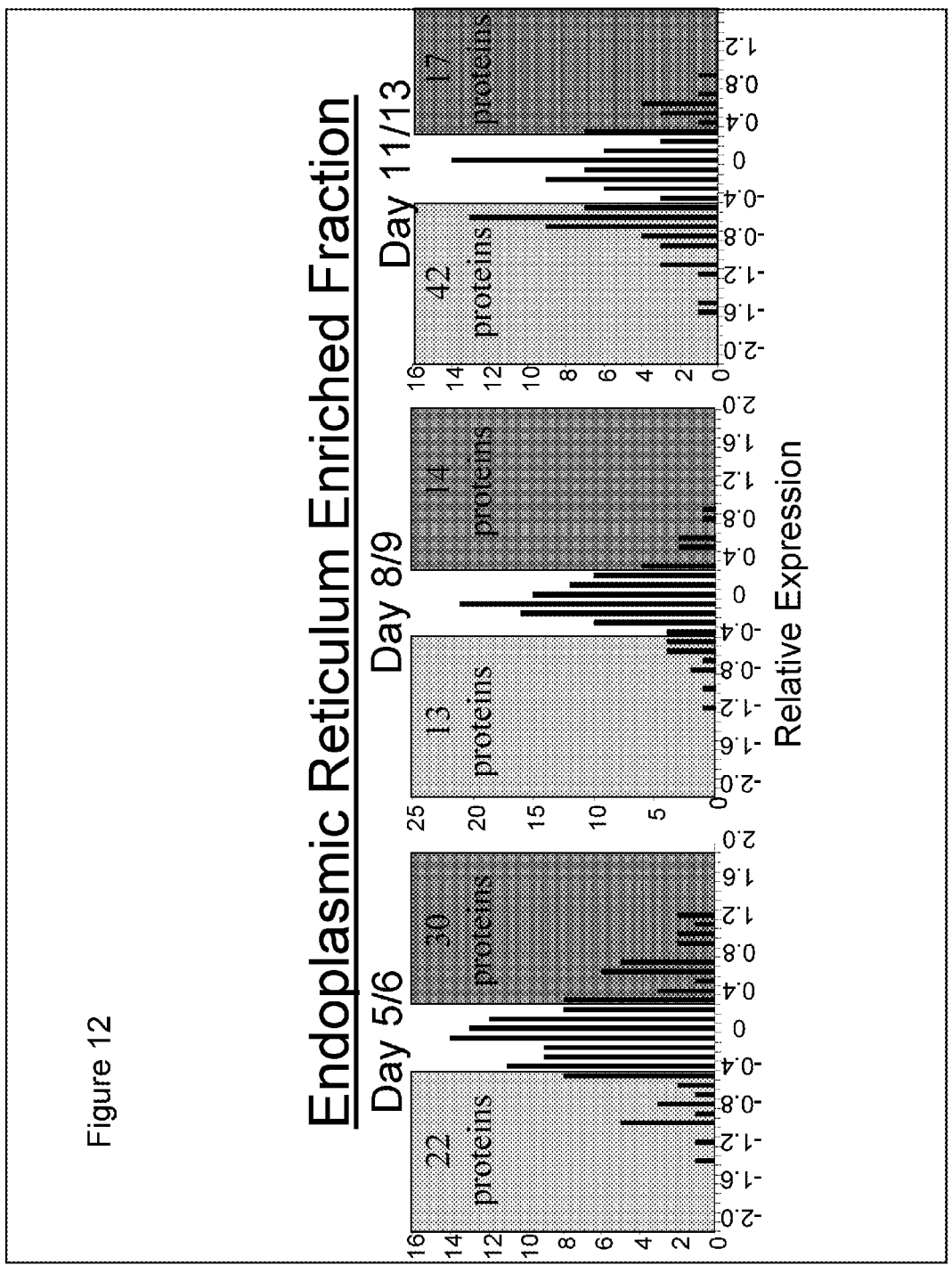
FIG. 12 depicts the relative expression (x-axis) versus number of proteins (y-axis) falling either less than −0.4 or greater than 0.4 in endoplasmic reticulum enriched fraction samples taken at days 5/6, 8/9, and 11/13 from the culture processes of Cell Line 3 described in Section 7.2.4.
Figure 13:
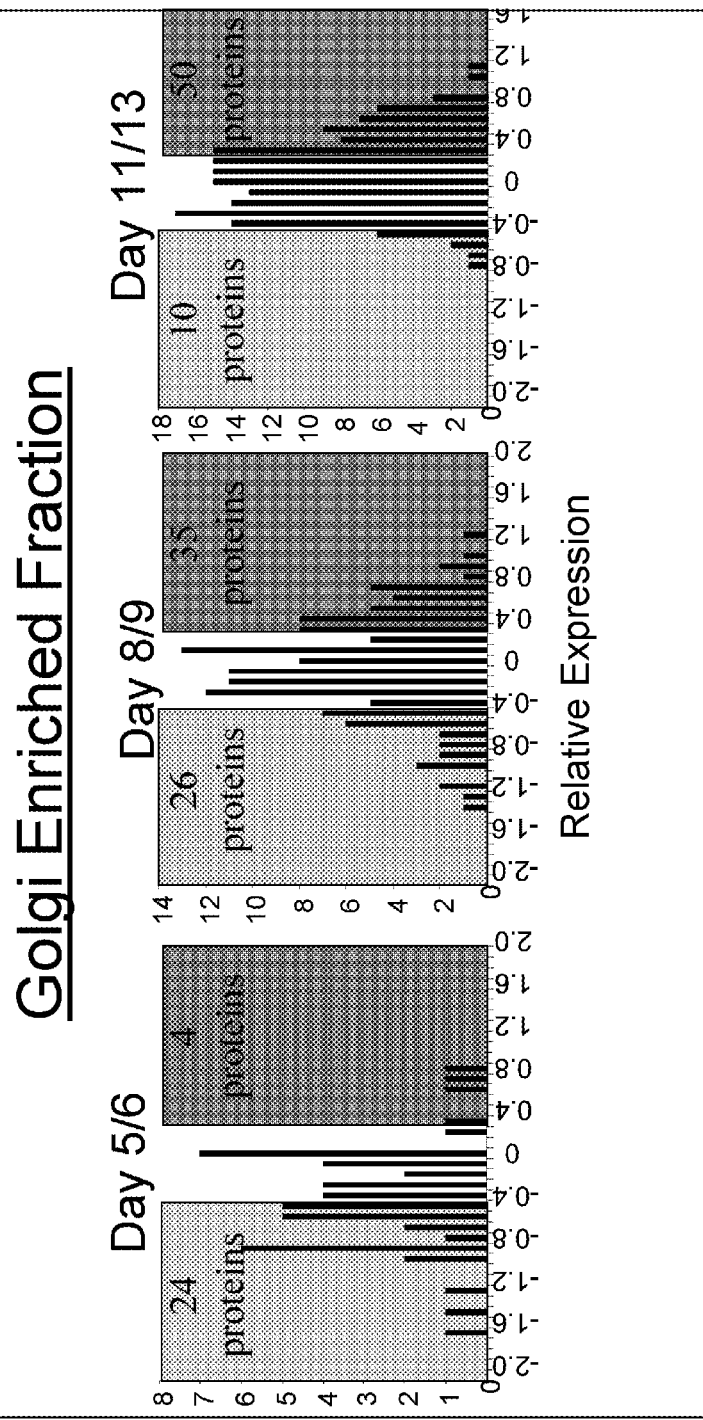
FIG. 13 depicts the relative expression (x-axis) versus number of proteins (y-axis) falling either less than −0.4 or greater than 0.4 in golgi reticulum enriched fraction samples taken at days 5/6, 8/9, and 11/13 from the culture processes of Cell Line 3 described in Section 7.2.4.

Cell Line 3 was cultured using two distinct process modes and two distinct culture media. Culture 1 of Cell Line 3 employed a batch process mode and a complex media. In contrast, Culture 2 of Cell Line 3 employed a fedbatch process mode and a chemically defined media. The relative values (Culture 1/Culture 2) of the product titer, specific productivity ($q_p$), and integral of viable cell density (IVC) for the Cell Line 3 comparison are provided in FIG. 11. To identify differentially expressed proteins samples of each culture were taken on Days 5/6, 8/9, and 11/13, and these samples were analyzed by 2-D gel electrophoresis. Summary data relating to the differentially expressed proteins is presented in FIGS. 12 (Endoplasmic Reticulum Enriched Fraction) and 13 (Golgi Enriched Fraction). Specific proteins identified as differentially expressed are presented in Table 6 (Endoplasmic Reticulum Enrich Fraction) and Table 7 (Golgi Enriched Fraction).

TABLE 6

Cell Line 3; Exemplary Differentially Expressed Proteins - ER Fraction

| Representative Proteins | Relative Expression (Sample Day) | Function |
| --- | --- | --- |
| Heat shock cognate 71 kDa protein | −1.41 (13) | Protein Folding |
| Major Vault Protein | −1.18 (9) | Signaling |
| Eukaryotic Translation Initiation Factor 5A-1 | −0.94 (6) | Protein Translation |

TABLE 7

Cell Line 3; Exemplary Differentially Expressed Proteins - Golgi Fraction

| Representative Proteins | Relative Expression (Sample Day) | Function |
|---|---|---|
| Guanine Nucleotide-Binding Protein | −1.32 (9) | Signaling |
| Heat Shock Protein Beta-1 | 1.24 (9) | Cellular Stress Response |
| 14-3-3 Protein Zeta/Delta | 0.96 (9) | Signaling |

All patents, patent applications, publications, product descriptions and protocols, cited in this specification are hereby incorporated by reference in their entirety. In case of a conflict in terminology, the present disclosure controls.

While it will be apparent that the invention herein described is well calculated to achieve the benefits and advantages set forth above, the present invention is not to be limited in scope by the specific embodiments described herein. It will be appreciated that the invention is susceptible to modification, variation and change without departing from the spirit thereof.

What is claimed is:

1. A method of identifying a high efficiency cell or cell culture comprising:
   (a) determining the expression level of a high efficiency cell or cell culture biomarker panel in the cell or cell culture, wherein said biomarker panel comprises guanine binding protein subunit beta 1, heat shock protein beta 1, and 14-3-3 protein zeta/delta, and
   (b) comparing the expression level of that high efficiency cell or cell culture biomarker panel in the cell or cell culture to the expression level of the biomarker panel in a known high efficiency cell or cell culture,
wherein an expression level of heat shock protein beta 1, and 14-3-3 protein zeta/delta higher than the level in the known high efficiency cell or cell culture and an expression level of guanine nucleotide binding protein subunit beta 1 less than the level in the known high efficiency cell or cell culture is indicative of a high efficiency cell or cell culture.

2. The method of claim 1 wherein the biomarker panel comprises an additional secretory protein.

3. The method of claim 2 wherein the additional secretory protein is an endoplasmic reticulum fraction-resident protein.

4. The method of claim 2 wherein the additional secretory protein is a Golgi fraction-resident protein.

5. The method of claim 2 wherein the additional secretory protein is up-regulated in a high efficiency cell or cell culture.

6. The method of claim 2 wherein the additional secretory protein is down-regulated in a high efficiency cell or cell culture.

7. The method of claim 2 wherein the level of multiple additional secretory proteins are determined and compared.

8. The method of claim 7 wherein all of the additional secretory proteins are down-regulated in the high efficiency cell or cell culture.

9. The method of claim 7 wherein all of the additional secretory proteins are up-regulated in the high efficiency cell or cell culture.

10. The method of claim 7 wherein one or more of the additional secretory proteins is up-regulated while one or more of the additional secretory proteins is down-regulated in the high efficiency cell or cell culture.

11. The method of claim 2 wherein the additional secretory protein is selected from the group consisting of: Endoplasmin precursor (GRP 94); Seryl-tRNA synthetase; Dihydrolipolyl-ysine residue acetyltransferase/methionineaminopeptidase 2; F-actin capping protein subunit alpha 2; 60s acidic ribosomal protein PO; Heterogeneous nuclear ribonucleoprotein K; Eukaryotic translation initiation factor 3 subunit 7; Endoplasmin precursor (GRP 94); Elongation factor 1 beta; Seryl-tRNA synthetase/RAS GTPase-activating protein binding 2; Eukaryotic translation factor 3 subunit 3; Pre mRNA processing factor 19/T-complex protein 1 subunit beta; Elongation factor 1 gamma; Tubulin gamma-1 chain/Eukaryotic translation initiation factor 2 subunit 2; Vimentin; Myosin regulatory light chain; 26S Protease regulatory subunit 6B; Eukaryotic peptide chain releases factor subunit 1; Protein disulfide isomerase A-3 precursor; Tubulin alpha-2; Endoplasmin precursor (GRP 94); Protein disulfide isomerase A-6 precursor/ Protein NDRG1 (N-myc downstream-regulated gene 1 protein); 60 kDa heat shock protein, mitochondrial precursor (Hsp60); T-complex protein 1 subunit epsilon; UPF0027 protein; 26S Proteasome non ATP-ase regulatory subunit 13; SH3 domain GRB2-like protein B1; COP9 sinalosome complex subunit 4; Cytoplasmic dynein 1 intermediate chain; Ribosome Binding Protein 1; Alcohol Dehydrogenase (NADP+); Glutamate dehydrogenase 1 (mitochondrial precursor); Proteasome activator complex subunit 1; Cytoplasmic 2, Actin; Annexin A5; Coatomer subunit Epsilon; Glucosidase 2; Triosephosphate isomerase; Heterogeneous nuclear ribonucleoprotein F; Cytoplasmic 2/Actin; Sorting Nexin 6/Synaptic vesicle membrane VAT-1 homolog; Vimentin/Tubulin alpha-2 chain; Vacuolar ATP Synthase; Ig-G gamma-1 chain C; EH-Domain Containing Protein 4; Translation Initiation Factor 3 Subunit 3; ATP Synthase Subunit Beta; 60S Acidic Ribosomal Protein PO; Ezrin; Nucleophosmin; Calreticulin; 14-3-3 Protein Gamma; Septin-11; Annexin A2; ADP-Ribosylation Factor-Like Protein 2R; Heat Shock Cognate 71 kDa Protein; Myosin Light Polypeptide 6; and Major Vault Protein.

12. A kit for identifying modulation in expression of a secretory protein biomarker of high efficiency protein expression comprising:
(a) multiple detectable antibodies and wherein each antibody specifically binds to a secretory protein of a biomarker panel of high efficiency protein expression, wherein the biomarker panel comprises guanine nucleotide binding protein subunit beta 1, heat shock protein beta 1, and 14-3-3 protein zeta/delta; and
(b) a means for detecting said antibody.

13. The kit of claim 12 comprising an additional detectable antibody directed against an additional secretory protein, wherein the additional secretory protein is selected from the group consisting of: Endoplasmin precursor (GRP 94); Seryl-tRNA synthetase; Dihydrolipolylysine residue acetyltransferase/methionineaminopeptidase 2; F-actin capping protein subunit alpha 2; 60s acidic ribosomal protein PO; Heterogeneous nuclear ribonucleoprotein K; Eukaryotic translation initiation factor 3 subunit 7; Endoplasmin precursor (GRP 94); Elongation factor 1 beta; Seryl-tRNA synthetase/RAS GTPase-activating protein binding 2; Eukaryotic translation factor 3 subunit 3; Pre mRNA processing factor 19/T-complex protein 1 subunit beta; Elongation factor 1 gamma; Tubulin gamma-1 chain/Eukaryotic translation initiation factor 2 subunit 2; Vimentin; Myosin regulatory light chain; 26S Protease regulatory subunit 6B; Eukaryotic peptide chain releases factor subunit 1; Protein disulfide isomerase A-3 precursor; Tubulin alpha-2; Endoplasmin precursor (GRP 94); Protein disulfide isomerase A-6 precursor/Protein NDRG1 (N-myc downstream-regulated gene 1 protein); 60 kDa heat shock protein, mitochondrial precursor (Hsp60); T-complex protein 1 subunit epsilon; UPF0027 protein; 26S Proteasome non ATP-ase regulatory subunit 13; SH3 domain GRB2-like protein B1; COP9 sinalosome complex subunit 4; Cytoplasmic dynein 1 intermediate chain; Ribosome Binding Protein 1; Alcohol Dehydrogenase (NADP+); Glutamate dehydrogenase 1 (mitochondrial precursor); Proteasome activator complex subunit 1; Cytoplasmic 2, Actin; Annexin A5; Coatomer subunit Epsilon; Glucosidase 2; Triosephosphate isomerase; Heterogeneous nuclear ribonucleoprotein F; Cytoplasmic 2/Actin; Sorting Nexin 6/Synaptic vesicle membrane VAT-1 homolog; Vimentin/Tubulin alpha-2 chain; Vaculoar ATP Synthase; Ig-G gamma-1 chain C; EH-Domain Containing Protein 4; Translation Initiation Factor 3 Subunit 3; ATP Synthase Subunit Beta; 60S Acidic Ribosomal Protein PO; Ezrin; Nucleophosmin; Calreticulin; 14-3-3 Protein Gamma; Septin-11; Annexin A2; ADP-Ribosylation Factor-Like Protein 2R; Heat Shock Cognate 71 kDa Protein; Myosin Light Polypeptide 6; and Major Vault Protein.

14. The kit of claim 13 wherein the kit comprises multiple additional detectable antibodies and wherein each antibody specifically binds to a different additional secretory protein selected from the group consisting of Endoplasmin precursor (GRP 94); Seryl-tRNA synthetase; Dihydrolipolylysine residue acetyltransferase/methionineaminopeptidase 2; F-actin capping protein subunit alpha 2; 60s acidic ribosomal protein PO; Heterogeneous nuclear ribonucleoprotein K; Eukaryotic translation initiation factor 3 subunit 7; Endoplasmin precursor (GRP 94); Elongation factor 1 beta; Seryl-tRNA synthetase/RAS GTPase-activating protein binding 2; Eukaryotic translation factor 3 subunit 3; Pre mRNA processing factor 19/T-complex protein 1 subunit beta; Elongation factor 1 gamma; Tubulin gamma-1 chain/Eukaryotic translation initiation factor 2 subunit 2; Vimentin; Myosin regulatory light chain; 26S Protease regulatory subunit 6B; Eukaryotic peptide chain releases factor subunit 1; Protein disulfide isomerase A-3 precursor; Tubulin alpha-2; Endoplasmin precursor (GRP 94); Protein disulfide isomerase A-6 precursor/Protein NDRG1 (N-myc downstream-regulated gene 1 protein); 60 kDa heat shock protein, mitochondrial precursor (Hsp60); T-complex protein 1 subunit epsilon; UPF0027 protein; 26S Proteasome non ATP-ase regulatory subunit 13; SH3 domain GRB2-like protein B1; COP9 sinalosome complex subunit 4; Cytoplasmic dynein 1 intermediate chain; Ribosome Binding Protein 1; Alcohol Dehydrogenase (NADP+); Glutamate dehydrogenase 1 (mitochondrial precursor); Proteasome activator complex subunit 1; Cytoplasmic 2, Actin; Annexin A5; Coatomer subunit Epsilon; Glucosidase 2; Triosephosphate isomerase; Heterogeneous nuclear ribonucleoprotein F; Cytoplasmic 2/Actin; Sorting Nexin 6/Synaptic vesicle membrane VAT-1 homolog; Vimentin/Tubulin alpha-2 chain; Vaculoar ATP Synthase; Ig-G gamma-1 chain C; EH-Domain Containing Protein 4; Translation Initiation Factor 3 Subunit 3; ATP Synthase Subunit Beta; 60S Acidic Ribosomal Protein PO; Ezrin; Nucleophosmin; Calreticulin; 14-3-3 Protein Gamma; Septin-11; Annexin A2; ADP-Ribosylation Factor-Like Protein 2R; Heat Shock Cognate 71 kDa Protein; Myosin Light Polypeptide 6; and Major Vault Protein.

15. The kit of claim 13 wherein the kit comprises a positive control sample.

16. The kit of claim 13 wherein the kit comprises a negative control sample.

* * * * *

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: synthetic peptide

<400> SEQUENCE: 1

Glu Gly Ile Pro Ala Gly Trp Gln Gly Leu Asp Asn Gly Pro Glu Ser
1               5                   10                  15

Arg Lys

<210> SEQ ID NO 2
<211> LENGTH: 340
<212> TYPE: PRT
<213> ORGANISM: Homo sapiens

<400> SEQUENCE: 2

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
                20                  25                  30

Ile Thr Asn Asn Ile Asp Pro Val Gly Arg Ile Gln Met Arg Thr Arg
            35                  40                  45

Arg Thr Leu Arg Gly His Leu Ala Lys Ile Tyr Ala Met His Trp Gly
        50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190
```

-continued

```
Ala Pro Asp Thr Arg Leu Phe Val Ser Gly Ala Cys Asp Ala Ser Ala
    195                 200                 205

Lys Leu Trp Asp Val Arg Glu Gly Met Cys Arg Gln Thr Phe Thr Gly
    210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
                260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
    290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340
```